United States Patent [19]
Wright

[11] Patent Number: 6,102,927
[45] Date of Patent: Aug. 15, 2000

[54] BLOOD LANCET AND METHOD OF MANUFACTURE

[76] Inventor: George A. Wright, 960 S. Massachusetts Ave., DeLand, Fla. 32724

[21] Appl. No.: 09/302,467

[22] Filed: Apr. 30, 1999

[51] Int. Cl.7 .................................................. A61B 17/34
[52] U.S. Cl. ............................................................ 606/181
[58] Field of Search .................................. 606/181, 182, 606/183, 184, 185

[56] References Cited

U.S. PATENT DOCUMENTS

| | | |
|---|---|---|
| 3,658,974 | 4/1972 | Low . |
| 3,970,490 | 7/1976 | Raines et al. . |
| 4,097,318 | 6/1978 | Olschewski . |
| 5,203,940 | 4/1993 | Krone . |
| 5,312,508 | 5/1994 | Chisholm . |
| 5,324,303 | 6/1994 | Strong et al. ............................ 606/181 |
| 5,386,571 | 1/1995 | Morita ..................................... 606/181 |
| 5,389,177 | 2/1995 | Shuert . |
| 5,397,621 | 3/1995 | Donzac et al. . |
| 5,399,215 | 3/1995 | Blot et al. . |
| 5,522,961 | 6/1996 | Leonhardt . |
| 5,569,286 | 10/1996 | Peckham et al. . |
| 5,913,868 | 6/1999 | Marshall et al. ........................ 606/181 |

*Primary Examiner*—Michael Buiz
*Assistant Examiner*—Kevin Truong
*Attorney, Agent, or Firm*—Paul S. Rooy

[57] ABSTRACT

A lancet and method of manufacture. The lancet comprises a wire sandwiched between an upper web and a lower web. A twist-off wire point cover is provided to protect the point of the wire, and to preserve its sterility until use. The method of manufacture includes the steps of heating the upper and lower webs, thermoforming a lower web wire groove and a lower web wire point recess into the lower web, loading a wire into the lower web wire groove such that its point is disposed within the lower web wire point recess, gluing the upper web to the lower web at a lidding station, and cutting twist-off slits into the upper and lower webs to provide the twist-off cover. Alternate embodiments of the lancet are disclosed which provide a lancet containing a valley to facilitate wire loading, and which provide finger grips on the upper and lower webs. A butterfly and method of manufacture are also disclosed.

16 Claims, 5 Drawing Sheets

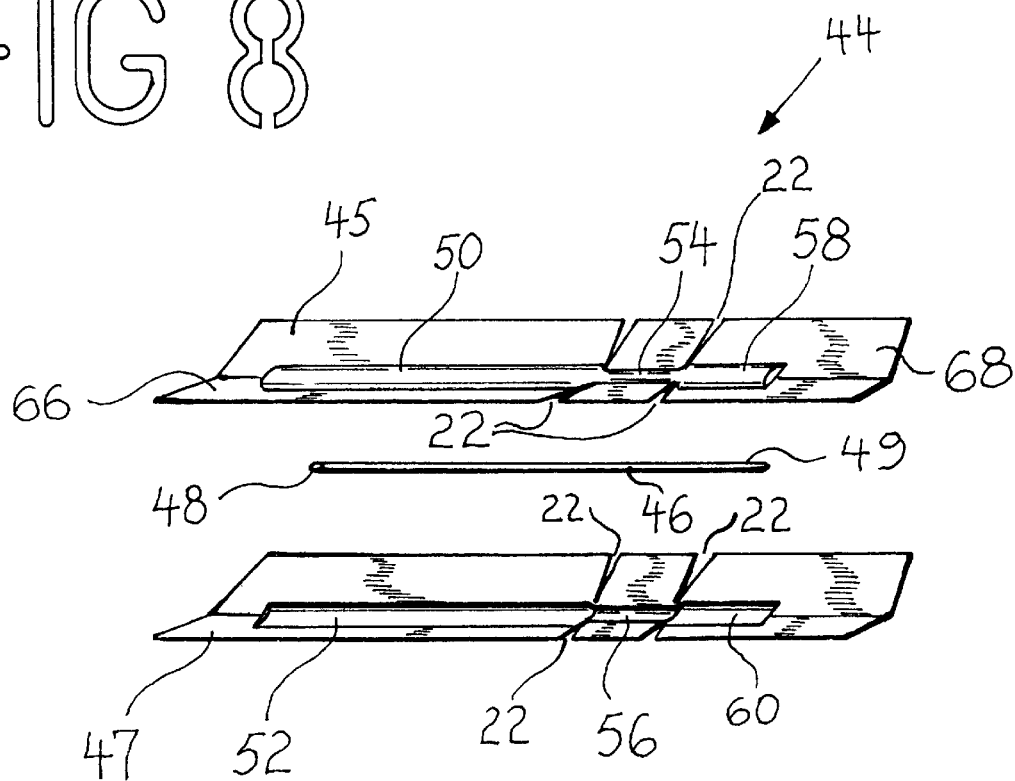
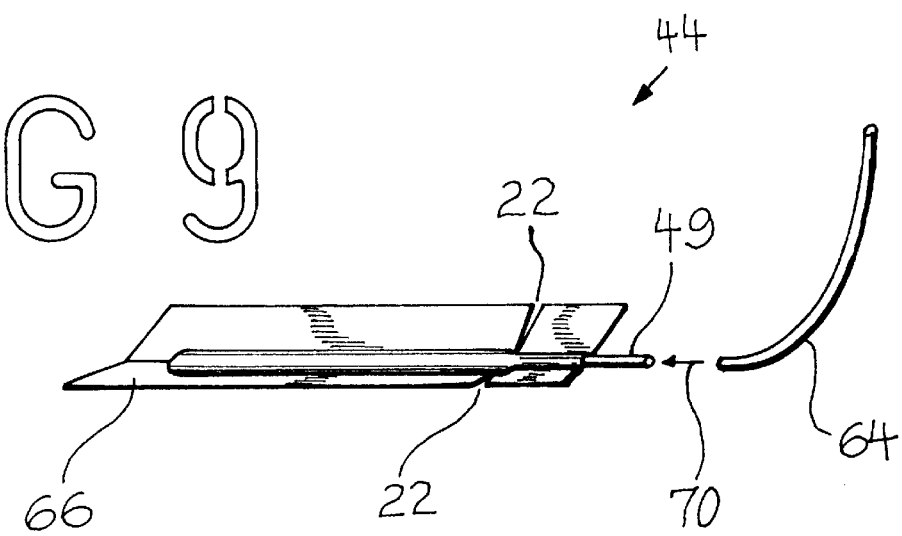

BLOOD LANCET AND METHOD OF MANUFACTURE

BACKGROUND OF THE INVENTION

1. Field of the Invention

This invention relates to blood lancets, and in particular to a thermoformed blood lancet and method of manufacture.

2. Background of the Invention

A small sample of blood is often required in diagnostic laboratories for analysis. This sample is frequently acquired by pricking the finger of the patient with a blood lancet. In the case of small individuals or infants the sample may be taken by pricking the heel or ear. In the case of diabetics, it may be necessary to take blood samples several times throughout the day for blood sugar analysis.

Conventional lancets comprise a wire secured to a holding device which is easily grasped between a thumb and finger. Lancets may also fit into an automatic pricking device.

Existing Designs

Blood lancets today are generally manufactured using either an injection-molding process or an assembly process. In the injection-molding process, the wire is held in place by the adherence of the wire to the surrounding finger grip material. The finger grips are generally made of plastic material such as polyethylene. The sharp point of the wire is embedded in a point cover with a narrow neck attaching the point cover to the finger grips. The point cover maintains the wire point clean until use. When the lancet is to be used, the point cover is twisted off at the neck, thus exposing the wire point for use.

The injection-molding process of blood lancet production suffers from a variety of disadvantages. The injection-molding machine costs approximately $150,000, the mold costs approximately $150,000, and the mold loading equipment another $100,000. All this equipment is dedicated—that is to say, it can only be used to manufacture a single product: the injection-molded blood lancet. Consequently, the currently available injection-molding lancets cost in the vicinity of $11–$13 per thousand.

The assembly process involves attaching the wire to the finger grips with an adhesive such as thermal epoxy, two-part epoxy, or UV adhesive. A cap is then placed over the wire point for protection and sterility. When the lancet is to be used, the cap is twisted off at the neck, thus exposing the wire point for use.

The assembly process of blood lancet manufacture also suffers from a variety of drawbacks. The mold could cost around $300,000–$500,000, and the assembly machine as much as $1,500,000. As in the injection-molding process, all this equipment is dedicated, and thus cannot be used to produce any product other than the blood lancet for which it was designed. This high equipment cost elevates the blood lancet cost using this manufacture method to $12–$14 per thousand.

SUMMARY OF THE INVENTION

Accordingly, it is an object of the present invention to provide a blood lancet and method of manufacture which produces lower-cost blood lancets. Design features allowing this object to be accomplished include the method steps of thermoforming an upper web and a lower web, loading a wire into the lower web, sealing the two together, and cutting out the individual blood lancets while simultaneously cutting twist-off slits into the webs. Advantages associated with the accomplishment of this object include a lower-cost blood lancet costing in the vicinity of $6–$7 per thousand, and the associated increased availability and affordability.

It is another object of the present invention to provide a blood lancet and method of manufacture which uses non-dedicated machinery in the manufacturing method. Design features allowing this object to be accomplished include the method steps of thermoforming an upper web and a lower web, loading a wire into the lower web, sealing the two together, and cutting out the individual blood lancets while simultaneously cutting twist-off slits into the webs. A benefit associated with the accomplishment of this object is the flexibility of being able to use the production machinery to produce other products.

It is still another object of this invention to provide a butterfly cannula and method of manufacture which produces lower-cost blood lancets. Design features allowing this object to be accomplished include the method steps of thermoforming an upper web and a lower web, loading a wire into the lower web, sealing the two together, cutting out the individual butterflies while simultaneously cutting twist-off slits into the webs, and finally attaching an IV tube to the cannula butt. Advantages associated with the accomplishment of this object include a lower-cost blood cannula, and the associated increased availability and affordability.

It is yet another object of the present invention to provide a butterfly cannula and method of manufacture which uses non-dedicated machinery in the manufacturing method. Design features allowing this object to be accomplished include the method steps of thermoforming an upper web and a lower web, loading a wire into the lower web, sealing the two together, and cutting out the individual butterflies while simultaneously cutting twist-off slits into the webs. A benefit associated with the accomplishment of this object is the flexibility of being able to use the production machinery to produce other products.

BRIEF DESCRIPTION OF THE DRAWINGS

The invention, together with the other objects, features, aspects and advantages thereof will be more clearly understood from the following in conjunction with the accompanying drawings.

Five sheets of drawings are provided. Sheet one contains FIGS. 1 and 2. Sheet two contains FIG. 3. Sheet three contains FIGS. 4 and 5. Sheet four contains FIGS. 6 and 7. Sheet five contains FIGS. 8 and 9.

FIG. 8 is a side exploded isometric view of a butterfly.

FIG. 9 is a side isometric view of a butterfly.

DETAILED DESCRIPTION OF THE PREFERRED EMBODIMENT

Figure 1:
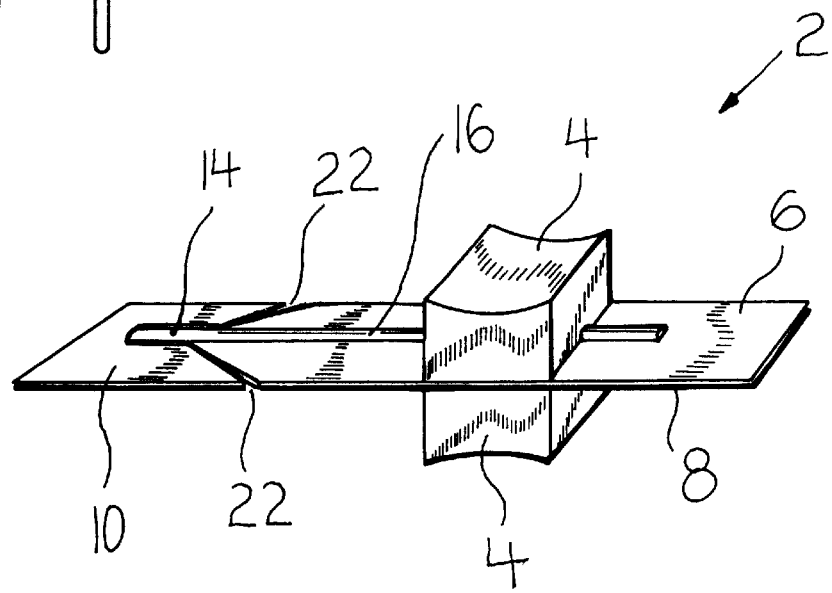
FIG. 1 is a side isometric view of a lancet.
Figure 2:
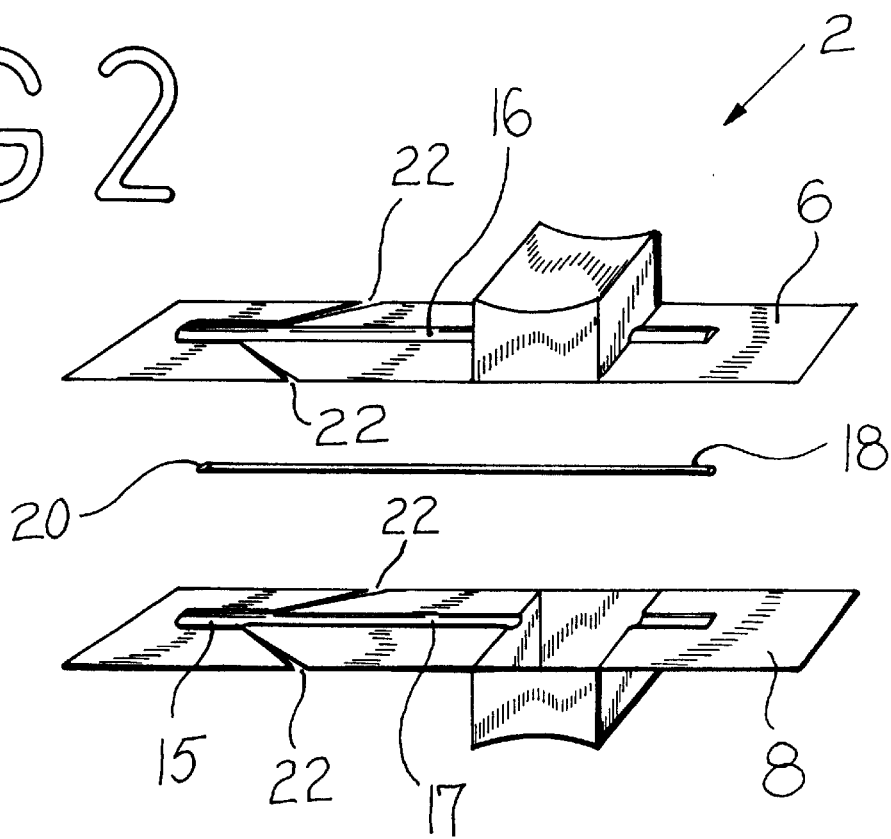
FIG. 2 is a side isometric exploded view of a lancet.

FIG. 1 is a side isometric view of lancet 2, and FIG. 2 is a side isometric exploded view of lancet 2. Lancet 2 comprises wire 18 sandwiched between an upper web 6 and a lower web 8. Upper web 6 comprises upper web wire groove 16 communicating with upper web wire point recess 14. Lower web 8 comprises lower web wire groove 17 communicating with lower web wire point recess 15. Upper web wire groove 16 is sized to admit the upper half of wire 18; lower web wire groove 17 is sized to admit the lower half of wire 18. Upper web wire point recess 14 and lower web wire point recess 15 are somewhat larger in cross-sectional area than upper web wire groove 16 and lower web wire groove 17. Upper web wire point recess 14 and lower web wire point recess 15 are sized to admit wire 18 plus a cushion of air surrounding wire 18.

Upper web 6 and lower web 8 each comprise a finger grip 4 to facilitate holding lancet 2 in use. Lancet 2 further comprises twist-off slits 22 extending from a side edge of lancet 2 almost to the intersections of upper wire web groove 16 with upper web wire point recess 14, and lower web wire groove 17 with lower web wire point recess 15. In this manner, a convenient "twist-off" wire point cover 10 is provided, which can be easily separated from the remainder of lancet 2 when lancet 2 is to be used. Prior to such use, wire point cover 10 forms an air-tight seal around wire point 20, thus preserving the sterility of wire point 20 pending its use in obtaining a blood sample.

Figure 3:
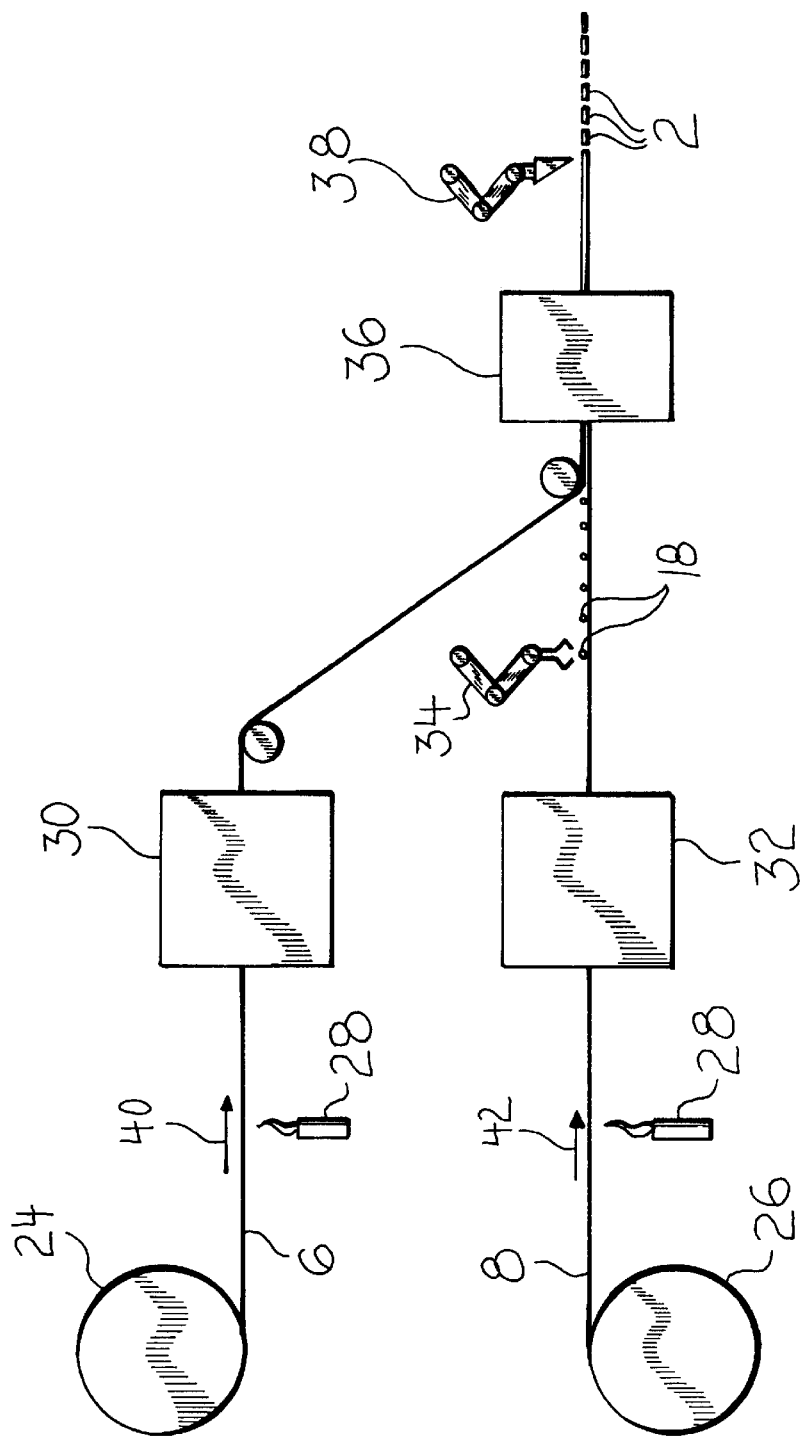
FIG. 3 is a schematic view of the instant method of manufacture of a lancet.

FIG. 3 is a schematic view of the instant method of manufacture of lancet 2. An upper web supply 24 and a lower web supply 26 simultaneously dispense upper web 6 material and lower web 8 material into respective heating stations having heat sources 28, as indicated by arrows 40 and 42. Upper web 6 material and lower web 8 material are thermoformable film material known in the art, such as PVC or Kodar, and may typically spend between 6 and 8 seconds being heated.

From the heating stations, upper web 6 material and lower web 8 material proceed to upper web thermoforming station 30 and lower web thermoforming station 32 respectively. Upper web thermoforming station 30 may thermoform upper web finger grip 4, upper web wire groove 16 and upper web wire point recess 14 into upper web 6. Lower web thermoforming station 32 thermoforms, lower web wire groove 17, lower web wire point recess 15, and (optionally) lower web finger grip 4, into lower web 8.

The thermoforming process is a known process which involves draping thermoformable film over a die, applying heat, and exposing the die-side of the thermoformable film to a vacuum. Atmospheric pressure pushes the thermoformable film into close conformity with the shape of the die. An assist die may optionally be employed against the non-vacuum side of the thermoformable material. Upon cooling, the thermoformable film retains the shape of the die(s).

Upon exiting lower web thermoforming station 32, the thermoformed lower webs 8 proceed to wire loading station 34, where a wire 18 is inserted into each lower web wire groove 17, with wire point 20 disposed within lower web wire point recess 15.

Thermoformed upper webs 6 and lower webs 8 then proceed into lidding station 36, indexed so that an upper web 6 is precisely superimposed upon, and co-extensive with, a corresponding lower web 8 containing a wire 18. The lower surface of upper web 6 material, the upper surface of lower web 8 material, or both, have been purchased pre-coated with an adhesive activated by heat and/or pressure. In lidding station 36, heat and/or pressure is applied to glue upper web 6 to lower web 8, and to glue wire 18 within upper web wire groove 16 and lower web wire groove 17.

Heat and/or pressure is applied via dies which apply heat and/or pressure so as to urge all portions of upper web 6 into close proximity with lower web 8, except for upper web wire point recess 14 and lower web wire point recess 15. Upper web wire point recess 14 and lower web wire point recess 15 are glued neither to each other nor to wire 18, in this fashion leaving an air cushion separating wire point 20 from upper web 6 and lower web 8, to facilitate a later "twist-off" of wire point cover 10.

From lidding station 36 the glued-together upper webs 6 and lower webs 8 proceed to cutting station 38, where twist-off slits 22 are cut, and the individual finished lancets 2 are cut apart.

It is important to note the instant method of manufacture may be completely automated, thus reducing the labor component of the finished lancet 2 cost. As another benefit, the instant form-lid-seal process can occur at a high speed. In addition, this method of manufacture permits use of a shorter wire, which is the most expensive component of the product. These factors all combine to permit the instant method to produce lancets 2 at a lower cost than any other lancets currently being manufactured using other methods.

Figure 6:
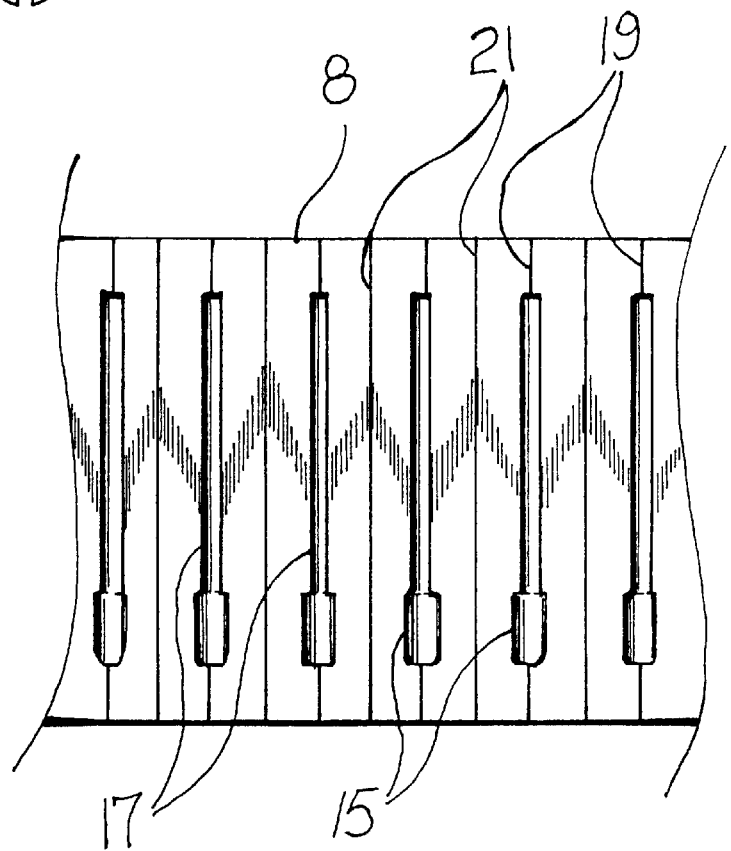
FIG. 6 is a plan view of a lower web sheet immediately following the lower web thermoforming production step.
Figure 7:
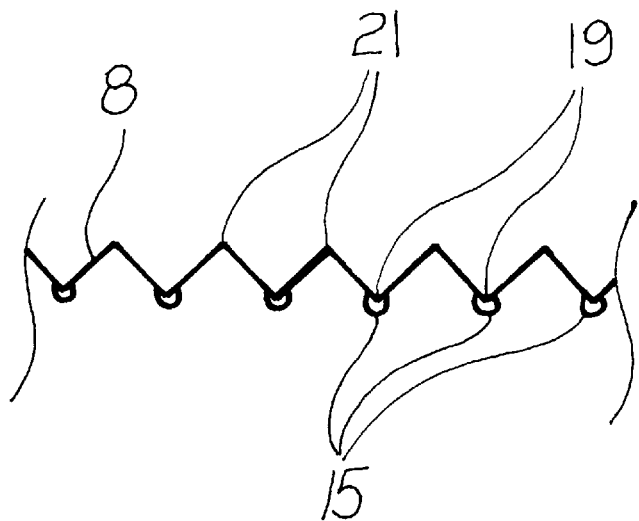
FIG. 7 is an end view of a lower web sheet immediately following the lower web thermoforming production step.

FIGS. 6 and 7 depict an alternate embodiment of lower web 8 material immediately following the thermoforming step. Lower web 8 material here comprises valleys 19 separated from each other by means of peaks 21. Lower web wire grooves 17 and lower web wire point recesses 15 are disposed in valleys 19. This configuration facilitates the loading of wires 18 in wire loading station 34: a wire 18 is simply dropped into a valley 19, and rolls down hill into lower web wire groove 17 and lower web wire point recess 15. This "valley and peak" cross-sectional shape of lower web 8 reduces the indexing accuracy required in wire loading station 34, thus further reducing manufacturing cost of lancets 2 produced by means of the instant method of manufacture.

Figure 4:
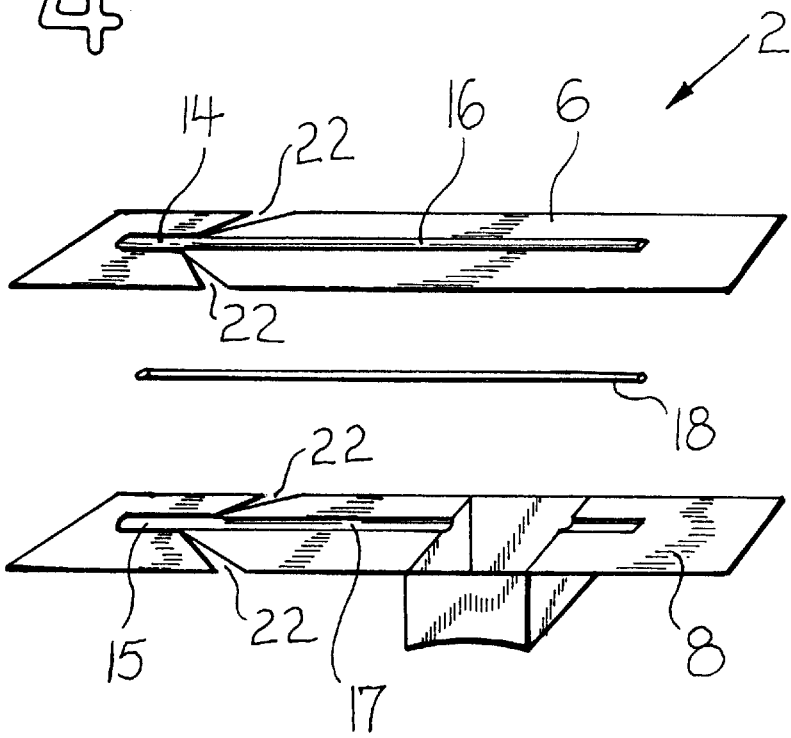
FIG. 4 is a side isometric exploded view of a first alternate embodiment of a lancet.

FIG. 4 is a side isometric exploded view of a first alternate embodiment of lancet 2. Lower web 8 is identical to the lower web 8 in the preferred embodiment lancet 2, but upper web 6 starts out as merely a flat, unthermoformed sheet. During the lidding step, the heat and/or pressure applied to upper web 6 causes it to conform somewhat to the contour of wire 18, thus producing abbreviated upper web wire groove 16 and upper web wire point recess 14 shapes. An important advantage to this first alternate embodiment of lancet 2 is the simplicity of manufacture: the only part which must be thermoformed is lower web 8. This simplicity of manufacture reduces the cost of production machinery, as well as the final per-unit cost, and has the potential for speeding production.

Figure 5:
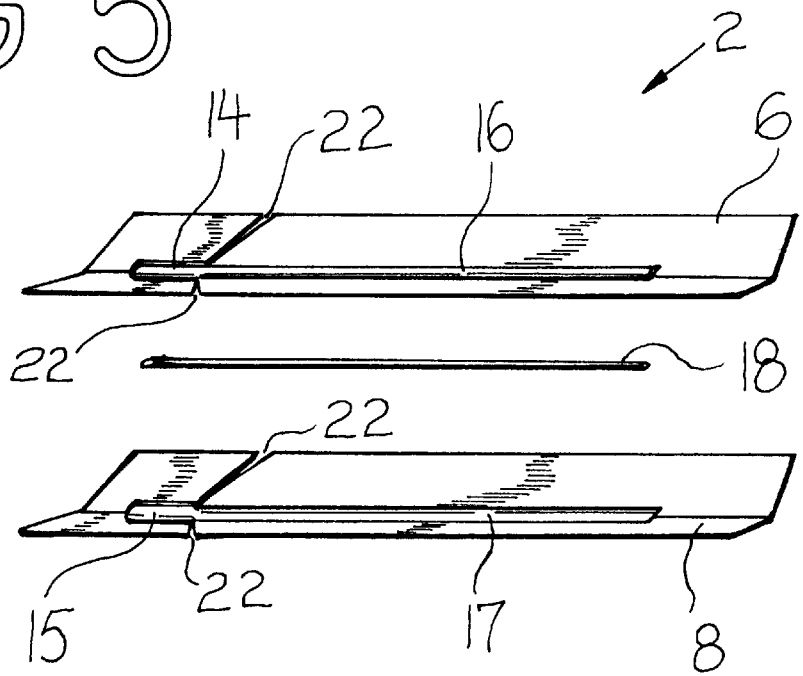
FIG. 5 is a side isometric exploded view of a second alternate embodiment of a lancet.

FIG. 5 is a side isometric exploded view of a second alternate embodiment of lancet 2 comprising a flat upper web 6 and a flat lower web 8. This second alternate embodiment of lancet 2 is identical to the first alternate embodiment of lancet 2 previously described, except lower web 8 does not have finger grip 4, and both upper web 6 and lower web 8 have the previously described valley 19. In lower web 8, valley 19 facilitates wire 18 placement. This second alternate embodiment of lancet 2 is a simpler design than the preferred embodiment, and thus enjoys lower tooling and manufacturing costs.

FIG. 8 is a side exploded isometric view of butterfly 44, and FIG. 9 is a side isometric view of a butterfly 44. Butterfly 44 is used in the insertion of an IV tube into a patient, and comprises hollow cannula 46 sandwiched between butterfly upper web 45 and butterfly lower web 47.

Cannula 46 comprises cannula point 48, which is the end inserted into a patient's vein. Cannula butt 49 is disposed at an extreme of cannula 46 opposite cannula point 48. Butterfly upper web 45 comprises upper web cannula groove 54 communicating at one extreme with upper web cannula point recess 50, and at an opposite extreme with upper web cannula butt recess 58. Butterfly lower web 47 comprises lower web cannula groove 56 communicating at one extreme with lower web cannula point recess 52, and at an opposite extreme with lower web cannula butt recess 60.

As in the lancet 2 embodiments, butterfly 44 comprises twist-off slits 22 extending from opposite side edges of butterfly 44 almost to the intersections of upper web cannula point recess 50 with upper web cannula groove 54, and lower web cannula point recess 52 with lower web cannula groove 56. These twist-off slits define a cannula point cover 66, which is twisted off from butterfly 44 prior to its use.

In addition, butterfly 44 comprises twist-off slits 22 extending from opposite side edges of butterfly 44 almost to the intersections of upper web cannula groove 54 with upper web cannula butt recess 58, and lower web cannula groove 56 with lower web cannula butt recess 60. These twist-off slits define a cannula butt cover 68, which is twisted off from butterfly 44 in order to attach IV tube 64 during the manufacturing process, as indicated by arrow 70 in FIG. 9. During manufacturing of butterfly 44, IV tube 64 may be glued to cannula butt 49 using adhesive such as cyanoacrilate or methylmetacholate.

Butterfly 44 may be manufactured same as in any of the three embodiments of lancet 2, with three exceptions.

First, during the thermoforming steps, lower web cannula butt recess 60 is thermoformed into butterfly lower web 47, and upper web cannula butt recess 58 is optionally thermoformed into butterfly upper web 45.

Second, during the lidding step, all of butterfly upper web 45 is urged into contact with butterfly lower web 47 under heat and/or pressure, except upper web cannula point recess 50 is not urged into contact with lower web cannula point recess 52, nor is upper web cannula butt recess 58 urged into contact with lower web cannula butt recess 60.

Third, two sets of twist-off slits are cut into butterfly 44 at cutting station 38. As in lancet 2, a first set of twist-off slits 22 is cut into butterfly 44 which extends from opposite side edges of butterfly 44 almost to the intersections of upper web cannula point recess 50 with upper web cannula groove 54, and lower web cannula point recess 52 with lower web cannula groove 56. These twist-off slits 22 define a cannula point cover 66, which is twisted off from butterfly 44 prior to its use.

In addition, in butterfly 44 a second set of twist-off slits 22 is cut into butterfly 44 which extends from opposite side edges of butterfly 44 almost to the intersections of upper web cannula groove 54 with upper web cannula butt recess 58, and lower web cannula groove 56 with lower web cannula butt recess 60. These twist-off slits define a cannula butt cover 68, which is twisted off from butterfly 44 in order to attach IV tube 64 during the manufacturing process, as indicated by arrow 70.

Other than these differences, butterfly 44 may be manufactured using any of the methods used to manufacture any of the embodiments of lancet 2.

While a preferred embodiment and alternate embodiments of the invention have been illustrated herein, it is to be understood that changes and variations may be made by those skilled in the art without departing from the spirit of the appending claims.

| DRAWING ITEM INDEX | |
| --- | --- |
| 2 | lancet |
| 4 | finger grip |
| 6 | upper web |
| 8 | lower web |
| 10 | wire point cover |
| 14 | upper web wire point recess |
| 15 | lower web wire point recess |
| 16 | upper web wire groove |
| 17 | lower web wire groove |
| 18 | wire |
| 19 | valley |
| 20 | wire point |
| 21 | peak |
| 22 | twist-off slit |
| 24 | upper web supply |
| 26 | lower web supply |
| 28 | heat source |
| 30 | upper web thermoforming station |
| 32 | lower web thermoforming station |
| 34 | wire loading station |
| 36 | lidding station |
| 38 | cutting station |
| 40 | arrow |
| 42 | arrow |
| 44 | butterfly |
| 45 | butterfly upper web |
| 46 | cannula |
| 47 | butterfly lower web |
| 48 | cannula point |
| 49 | cannula butt |
| 50 | upper web cannula point recess |
| 52 | lower web cannula point recess |
| 54 | upper web cannula groove |
| 56 | lower web cannula groove |
| 58 | upper web cannula butt recess |
| 60 | lower web cannula butt recess |
| 64 | IV tube |
| 66 | cannula point cover |
| 68 | cannula butt cover |
| 70 | arrow |

I claim:

1. A lancet comprising a wire sandwiched between an upper web and a lower web, said lower web having been thermoformed to contain a lower web wire groove communicating with a lower web wire point recess, said wire comprising a wire point, said wire being disposed within and attached to said lower web wire groove by means of adhesive, said wire point being disposed within, but not being attached to, said lower web wire point recess, and a pair of twist-off slits cut into the upper and lower webs extending from opposite side edges of said lancet almost to an intersection of said lower web wire point recess with said lower web wire groove, said twist-off slits defining a twist-off wire point cover.

2. The lancet of claim 1 wherein said upper web and said lower web are substantially co-extensive and attached to each other and to that portion of said wire which is not said wire point by means of adhesive which is activated by means of pressure and/or heat.

3. The lancet of claim 2 wherein said lancet is divided into longitudinal halves along a centerline of said wire, and each said half is at an angle to the other said half, whereby location of said wire may be facilitated during a manufacturing process of said lancet.

4. The lancet of claim 2 wherein said lower web further comprises a thermoformed finger grip, whereby said lancet is easier to use.

5. The lancet of claim 2 wherein said upper web comprises an upper web wire groove communicating with an upper web wire point recess, said wire being disposed within and attached to said upper web wire groove by means of adhesive, said wire point being disposed within, but not being attached to, said upper web wire point recess.

6. The lancet of claim 5 wherein said upper web further comprises a thermoformed finger grip, whereby said lancet is easier to use.

7. The lancet of claim 5 wherein said upper web wire point recess is of a greater cross-sectional area than said upper web wire groove, and wherein said lower web wire point recess is of a greater cross-sectional area than said lower web wire groove, whereby an air cushion is created between said wire point and said upper web wire point recess and between said wire point and said lower web wire point recess.

8. A method of producing a lancet, said lancet comprising a wire sandwiched between an upper web and a lower web, said lower web having been thermoformed to contain a lower web wire groove communicating with a lower web wire point recess, said wire comprising a wire point, said wire being disposed within and attached to said lower web wire groove by means of adhesive, said wire point being disposed within, but not being attached to, said lower web point recess, and a pair of twist-off slits extending from opposite side edges of said lancet almost to an intersection of said lower web wire point recess with said lower web wire groove, said twist-off slits defining a twist-off wire point cover, said method comprising the steps of:

A. heating said lower web;
B. thermoforming said lower web wire groove communicating with said lower web wire point recess into said lower web;
C. loading said wire into said lower web wire groove and said lower web wire point recess such that said wire point is disposed within said lower web wire point recess;
D. applying heat and/or pressure to adhesive disposed on an upper surface of said lower web or on a lower surface of said upper web or both, said heat and/or pressure urging said lower web into contact with said upper web, said heat and/or pressure being applied to all of said upper web and all of said lower web except for said lower web wire point recess, and except for an upper web area co-extensive with said lower web wire point recess; and
E. cutting a pair of twist-off slits into the upper and lower webs extending from opposite side edges of said lancet almost to an intersection of said lower web wire point recess with said lower web wire groove.

9. The method of claim 8 comprising a further step of thermoforming a valley into said lower web whereby placement of said wire will be facilitated.

10. The method of claim 8 comprising a further steps of thermoforming a finger grip into said upper web whereby use of said lancet may be rendered easier.

11. The method of claim 8 comprising the further steps of thermoforming an upper web wire groove and an upper web wire point recess into said upper web, said wire point being disposed within, but not being attached to, said upper web point recess, and attaching a portion of said wire which is not said wire point to said upper web wire groove by means of adhesive.

12. The method of claim 11 comprising a further step of thermoforming a finger grip into said upper web.

13. A thermoformed butterfly comprising a cannula sandwiched between a butterfly upper web and a butterfly lower web, said butterfly lower web having been thermoformed to contain a lower web cannula groove communicating with a lower web cannula point recess, said cannula comprising a cannula point, said cannula being disposed within and attached to said lower web cannula groove by means of adhesive, said cannula point being disposed within, but not being attached to, said lower web cannula point recess, a pair of twist-off slits extending from opposite side edges of said cannula almost to an intersection of said lower web cannula point recess with said lower web cannula groove, said twist-off slits defining a twist-off cannula point cover, and an IV tube attached to an extreme of said cannula opposite said cannula point.

14. The thermoformed butterfly of claim 13 wherein said butterfly upper web comprises an upper web cannula groove communicating with an upper web cannula point recess, said cannula being disposed within and attached to said upper web cannula groove by means of adhesive, said cannula point being disposed within, but not being attached to, said upper web cannula point recess.

15. A method of manufacture of a butterfly, said butterfly comprising a cannula sandwiched between a butterfly upper web and a butterfly lower web, said butterfly lower web having been thermoformed to contain a lower web cannula groove communicating with a lower web cannula point recess, said cannula comprising a cannula point at one extreme and a cannula butt at an opposite extreme, said cannula being disposed within and attached to said lower web cannula groove by means of adhesive, said cannula point being disposed within, but not being attached to, said lower web cannula point recess, a pair of twist-off slits extending from opposite side edges of said cannula almost to an intersection of said lower web cannula point recess with said lower web cannula groove, said twist-off slits defining a twist-off cannula point cover, and an IV tube attached to said cannula butt, said method comprising the steps of:

A. heating said butterfly lower web and said butterfly upper web;
B. thermoforming said butterfly lower web to contain said lower web cannula groove, said lower web cannula point recess, and a lower web cannula butt recess;
C. loading a cannula into said lower web cannula groove, said lower web cannula point recess and said lower web cannula butt recess such that said cannula point is disposed within said lower web cannula point recess and said cannula butt is disposed within said lower web cannula butt recess;
D. applying heat and/or pressure to adhesive disposed on an upper surface of said butterfly lower web or on a lower surface of said butterfly upper web or both, said heat and/or pressure urging said butterfly lower web into contact with said butterfly upper web, said heat and/or pressure being applied to all of said butterfly upper web and all of said butterfly lower web except for said lower web cannula point recess and said lower web cannula butt recess, and except for upper web areas co-extensive with said lower web wire point recess and said lower web cannula butt recess;
E. cutting a first pair of twist-off slits into said butterfly upper web and said butterfly lower web extending from opposite side edges of said butterfly almost to an intersection of said lower web cannula point recess with said lower web cannula groove, said first pair of twist-off slits defining a cannula point cover, and cutting a second pair of twist-off slits into said butterfly upper web and said butterfly lower web extending from opposite side edges of said butterfly almost to an intersection of said lower web cannula butt recess with said lower web cannula groove, said second pair of twist-off slits defining a cannula butt cover;

F. twisting off said cannula butt cover; and

G. attaching an IV tube to said cannula butt.

16. The method of claim 15 comprising the further steps of thermoforming an upper web cannula point recess, an upper web cannula groove, and an upper web cannula butt recess into said butterfly upper web, said upper web cannula point recess communicating with and being disposed at one extreme of said upper web cannula groove, and said upper web cannula butt recess communicating with and being disposed at an extreme of said upper web cannula groove opposite said upper web cannula point recess.

* * * * *